United States Patent
Schmidt et al.

(10) Patent No.: US 9,853,743 B2
(45) Date of Patent: Dec. 26, 2017

(54) SYSTEMS AND METHODS FOR COMMUNICATION BETWEEN MEDICAL DEVICES

(71) Applicant: Cardiac Pacemakers, Inc., St. Paul, MN (US)

(72) Inventors: Brian L. Schmidt, White Bear Lake, MN (US); Lance Eric Juffer, Lino Lakes, MN (US); Keith R. Maile, New Brighton, MN (US); Michael J. Kane, St. Paul, MN (US); Brendan Early Koop, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/239,484

(22) Filed: Aug. 17, 2016

(65) Prior Publication Data
US 2017/0054516 A1 Feb. 23, 2017

Related U.S. Application Data

(60) Provisional application No. 62/207,686, filed on Aug. 20, 2015.

(51) Int. Cl.
*H04B 5/00* (2006.01)
*H04B 13/00* (2006.01)
(Continued)

(52) U.S. Cl.
CPC ......... *H04B 13/005* (2013.01); *A61B 5/0028* (2013.01); *A61B 5/0031* (2013.01);
(Continued)

(58) Field of Classification Search
None
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318, 11/2014, Jacobson et al. (withdrawn)
(Continued)

*Primary Examiner* — Tuan A Tran
(74) *Attorney, Agent, or Firm* — Seager, Tufte & Wickhem LLP

(57) ABSTRACT

Systems and methods for conducted communication are described. In one embodiment, a method of communicating with a medical device implanted within a patient comprises receiving, at a medical device via electrodes connected to the patient, a conducted communication signal, wherein the conducted communication signal comprises a signal component and a noise component. The method may further comprise adjusting, by the medical device, a receive threshold based at least in part on an amplitude of the received conducted communication signal so as to reduce an amplitude of the noise component of the conducted communication signal.

19 Claims, 14 Drawing Sheets

(51) Int. Cl.
*H04B 17/318* (2015.01)
*A61B 5/00* (2006.01)
*H04L 29/08* (2006.01)
*H04W 76/04* (2009.01)
*A61N 1/375* (2006.01)
*A61N 1/372* (2006.01)

(52) U.S. Cl.
CPC ...... *A61N 1/37211* (2013.01); *A61N 1/37223* (2013.01); *A61N 1/37252* (2013.01); *H04B 17/318* (2015.01); *H04L 67/12* (2013.01); *H04W 76/045* (2013.01); *A61N 1/3756* (2013.01); *A61N 1/37205* (2013.01); *A61N 1/37217* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,171 A * | 4/1999 | Wickham ............... A61B 5/042 128/901 |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |

(56) References Cited

U.S. PATENT DOCUMENTS

| | | |
|---|---|---|
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kadhiresan et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |

(56) References Cited

U.S. PATENT DOCUMENTS

| | | |
|---|---|---|
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | HüBinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 3,010,209 A1 | 8/2011 | Jacobson |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |

(56) References Cited

U.S. PATENT DOCUMENTS

| | | |
|---|---|---|
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |

(56) References Cited

U.S. PATENT DOCUMENTS

| | | |
|---|---|---|
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |

(56) References Cited

U.S. PATENT DOCUMENTS

| | | |
|---|---|---|
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0204758 A1 | 8/2010 | Boon et al. |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160557 A1 | 6/2011 | Cinbis et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |

(56) References Cited

U.S. PATENT DOCUMENTS

| | | |
|---|---|---|
| 2012/0109148 A1 | 5/2012 | Bonner et al. |
| 2012/0109149 A1 | 5/2012 | Bonner et al. |
| 2012/0109236 A1* | 5/2012 | Jacobson ............... A61N 1/368 607/4 |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1* | 11/2012 | Ellingson ............. A61N 1/3718 600/509 |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057563 A1* | 2/2015 | Kowalski ........... A61B 5/04001 600/554 |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |

(56) References Cited

U.S. PATENT DOCUMENTS

| | | |
|---|---|---|
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

International Search Report and Written Opinion for Application No. PCT/US2016/047386, 11 pages, dated Nov. 23, 2016.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, Jan. 29, 2016, 15 pages.

Spickler et al., "Totally Self-Contained Intracardiac Pacemaker," Journal of Electrocardiology, vol. 3(384): 324-331, 1970.

"Instructions for Use System 1, Leadless Cardiac Pacemaker (LCP) and Delivery Catheter," Nanostim Leadless Pacemakers, pp. 1-28, 2013.

\* cited by examiner

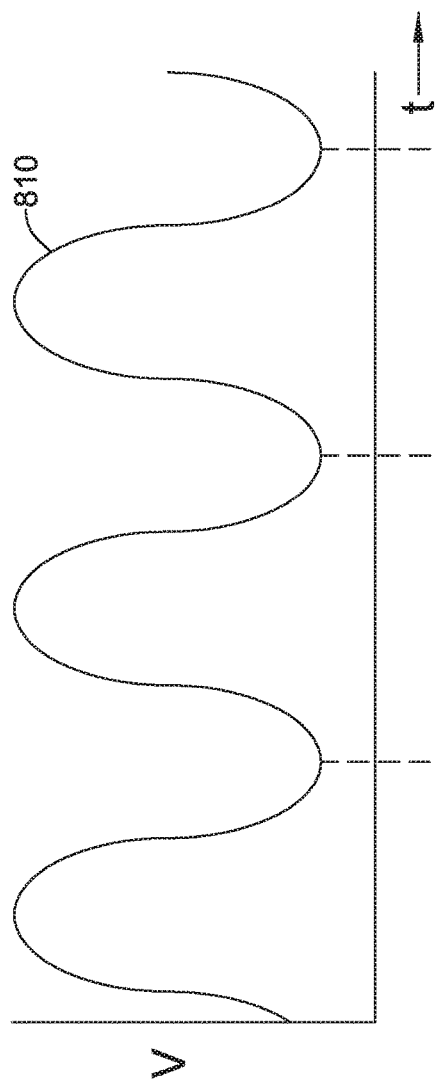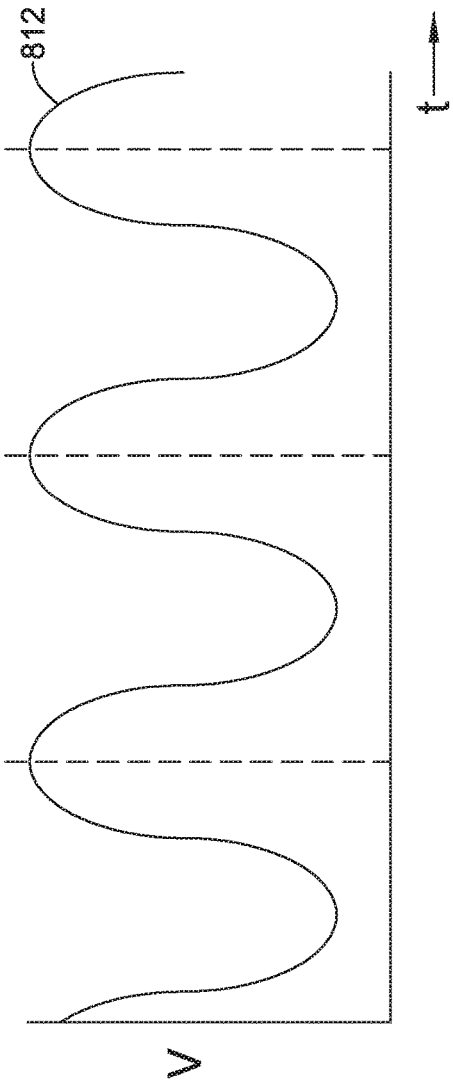

SYSTEMS AND METHODS FOR COMMUNICATION BETWEEN MEDICAL DEVICES

CROSS REFERENCE TO RELATED APPLICATIONS

This application claims the benefit of U.S. Provisional Patent Application Ser. No. 62/207,686 filed on Aug. 20, 2015, the disclosure of which is incorporated herein by reference.

TECHNICAL FIELD

The present disclosure generally relates to systems, devices, and methods for communicating between medical devices, and more particularly, to systems, devices, and methods for communicating between medical devices using conducted communication.

BACKGROUND

Active implantable medical devices are routinely implanted with a patient's body. Such implantable medical devices are often used to provide therapy, diagnostics or both. In some cases, it can be desirable to communicate with such implantable medical devices via the skin, such as via a programmer or the like located outside of the body. Such communication can be though conducted communication, which conducts electrical current through the patient's body tissue from one device to the other. In the programmer example, the programmer may be electrically connected to the patient's body through electrode skin patches or the like. Such communication may facilitate the programmer in programming and/or re-programming the implantable medical device, reading data collected by the implantable medical device, and/or collecting or exchanging any other suitable information. In some instances, two or more implantable medical devices may be implanted with a patient. In such cases, it can be desirable to establish communication between the two or more implanted medical devices using conducted communication. Such communication may facility the implanted medical devices in sharing data, distribution of control and/or delivery of therapy, and/or in performing other desired functions. These are just some example uses of conducted communication in the body.

SUMMARY

The present disclosure generally relates to systems, devices, and methods for communicating between medical devices, and more particularly, to systems, devices, and methods for communicating between medical devices using conducted communication.

In one embodiment, a method of communicating with a medical device implanted within a patient may comprise receiving, at a medical device via electrodes connected to the patient, a conducted communication signal, wherein the conducted communication signal comprises a signal component and a noise component. In some additional embodiments, the method may further include adjusting, by the medical device, a receive threshold based at least in part on an amplitude of the received conducted communication signal, and wherein adjusting the receive threshold at least partially reduce an amplitude of the noise component of the conducted communication signal.

Additionally, or alternatively, in any of the above described embodiments, adjusting the receive threshold based at least in part on the amplitude of the received conducted communication signal may comprise: counting, by the medical device, a number of pulses in the conducted communication signal having an amplitude greater than the receive threshold the during a communication window, determining, by the medical device, whether the counted number of pulses exceeds a pulse count threshold, and after determining the counted number of pulses exceeds the pulse count threshold, increasing, by the medical device, the receive threshold.

Additionally, or alternatively, any of the above described embodiments may further comprise increasing the receive threshold by a predetermined amount.

Additionally, or alternatively, in any of the above described embodiments, the pulse count threshold may represent a maximum number of pulses that may form a message.

Additionally, or alternatively, any of the above described embodiments may further comprise, after determining the counted number of pulses exceeds the pulse count threshold, beginning, by the medical device, a new communication window.

Additionally, or alternatively, any of the above described embodiments may further comprise, by the medical device: tracking a communication session timer, and after determining the communication session timer has reached a threshold value, setting, by the medical device, the receive threshold to a lower predetermined value.

Additionally, or alternatively, any of the above described embodiments may further comprise resetting, by the medical device, the communication session timer after successfully receiving a message.

Additionally, or alternatively, in any of the above described embodiments, adjusting the receive threshold based at least in part on an amplitude of the received conducted communication signal may comprise: after a communication window timer reaches a threshold value, determining, by the medical device, whether a message was received before the communication window timer reached the threshold value, wherein the message represents a predefined sequence of pulses in the communication signal having an amplitude above the receive threshold, and, after determining that no message was received before the communication window timer reached the threshold value, increasing, by the medical device, the receive threshold.

Additionally, or alternatively, in any of the above described embodiments, increasing the receive threshold may comprise increasing the receive threshold by a predetermined amount.

Additionally, or alternatively, any of the above described embodiments may further comprise: before the communication window timer has reached the threshold value, determining, by the medical device, whether a message has been received, and, after determining that a message has been received before the communication window timer has reached the threshold value, resetting, by the medical device, the communication window timer value.

Additionally, or alternatively, any of the above described embodiments, may further comprise: tracking, by the medical device, a communication session timer, and after determining that the communication session timer has reached a threshold value, setting, by the medical device, the receive threshold to a lower predetermined value.

Additionally, or alternatively, any of the above described embodiments may further comprise resetting, by the medical device, the communication session timer after determining that a message has been received.

Additionally, or alternatively, in any of the above described embodiments, adjusting the receive threshold based at least in part on an amplitude of the received conducted communication signal may comprise setting, by the medical device, the receive threshold to a value proportional to a maximum amplitude of a pulse of the communication signal having an amplitude above the receive threshold.

Additionally, or alternatively, in any of the above described embodiments, setting the receive threshold to a value proportional to the maximum amplitude of a pulse of the communication signal having an amplitude above the receive threshold may comprise setting the receive threshold to the maximum value of the amplitude of the pulse of the communication signal having an amplitude above the receive threshold.

Additionally, or alternatively, any of the above described embodiments may further comprising setting, by the medical device, the receive threshold to a value proportional to a maximum amplitude of each pulse of the communication signal having an amplitude above the receive threshold.

Additionally, or alternatively, in any of the above described embodiments, the receive threshold may decay according to a predetermined function.

In other embodiment, a medical device may comprise one or more electrode, and a controller connected to the one or more electrodes. In some of these embodiments, the controller may be configured to receive a signal comprising a conducted communication signal communicated from an external medical device and noise signals via the one or more electrodes and adjust the receive threshold based at least in part on an amplitude of the conducted communication signal and the noise signals to filter out noise signals from the received signal.

Additionally, or alternatively, in any of the above described embodiments, the controller may be further configured to adjust the receive threshold by setting the receive threshold to a value proportional to a maximum amplitude of each pulse of the received signal that exceeds the receive threshold.

Additionally, or alternatively, in any of the above described embodiments, the receive threshold may be configured to decay according to a predetermined decay function.

In still another embodiment, a medical device may comprise one or more electrodes, and a controller connected to the one or more electrodes. In some of these embodiments, the controller may be configured to receive a conducted communication signal via the one or more electrodes during a communication window and count a number of pulses of the conducted communication signal within the communication window and having an amplitude greater than a receive threshold. Additionally, the controller may be further configured to, if the pulse count reaches a pulse count threshold, increase the receive threshold and begin a new communication window.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 11A depicts an example patch-integrity signal;

FIG. 11B depicts an example cancelling or inverse signal which may be generated by a medical device such as the illustrative medical devices and medical device systems described with respect to FIGS. 1-4, in accordance with the techniques disclosed herein;

Figure 1:
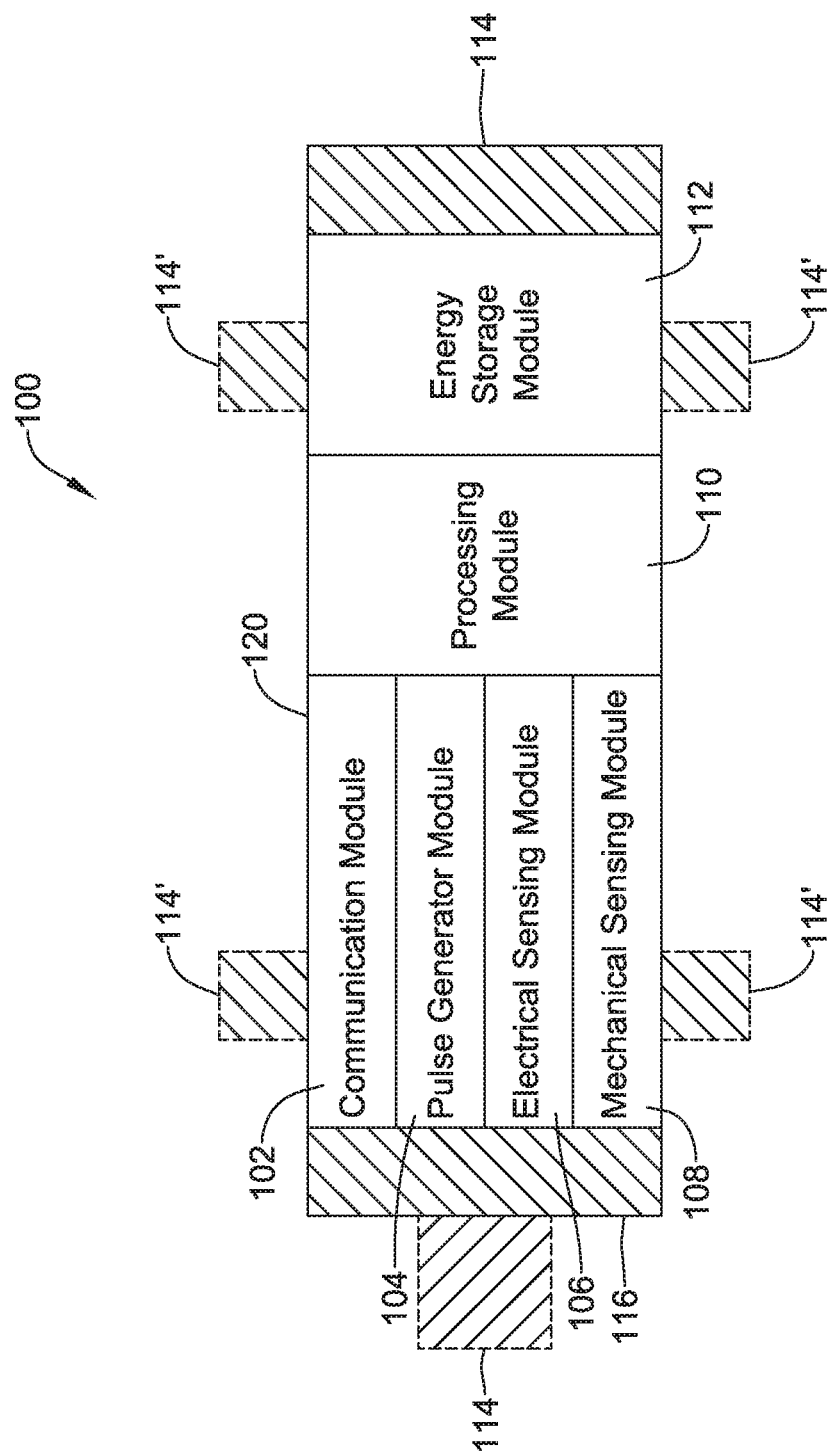
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for communicating between medical devices. Some medical device systems of the present disclosure may communicate using conducted communication techniques, which may include delivering electrical communication signals into a body of a patient for conduction through the patient's body. This signal may be received by another medical device, thereby establishing a communication link between the devices.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114. While a leadless cardiac pacemaker (LCP) is used as an example implantable medical device, it is contemplated that any suitable implantable medical device may be used, including implantable medical devices that provide therapy (e.g. pacing, neuro-stimulation, etc.), diagnostics (sensing), or both.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neuro-stimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias. Processing module 110 may further receive information from communication module 102. In some embodiments, processing module 110 may additionally use such received information to determine occurrences and types of arrhythmias. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator 104 generates electrical stimulation pulses.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

Figure 2:
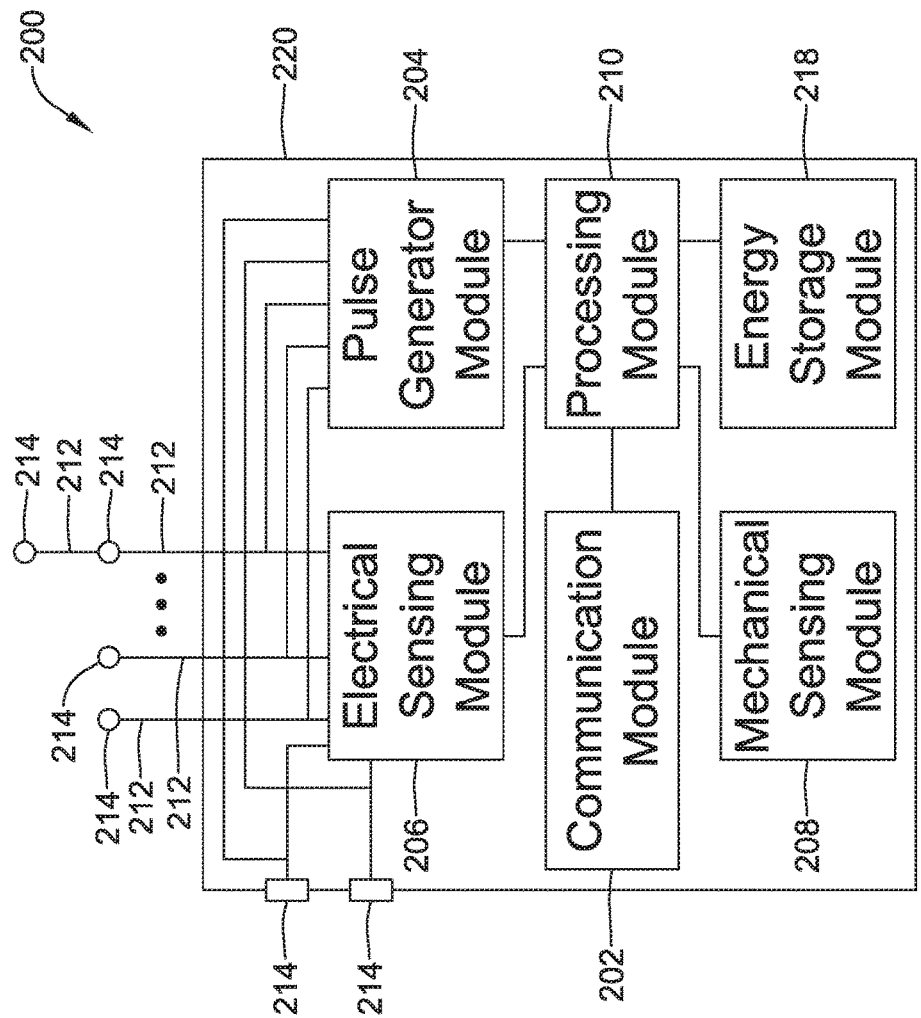
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and/or deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
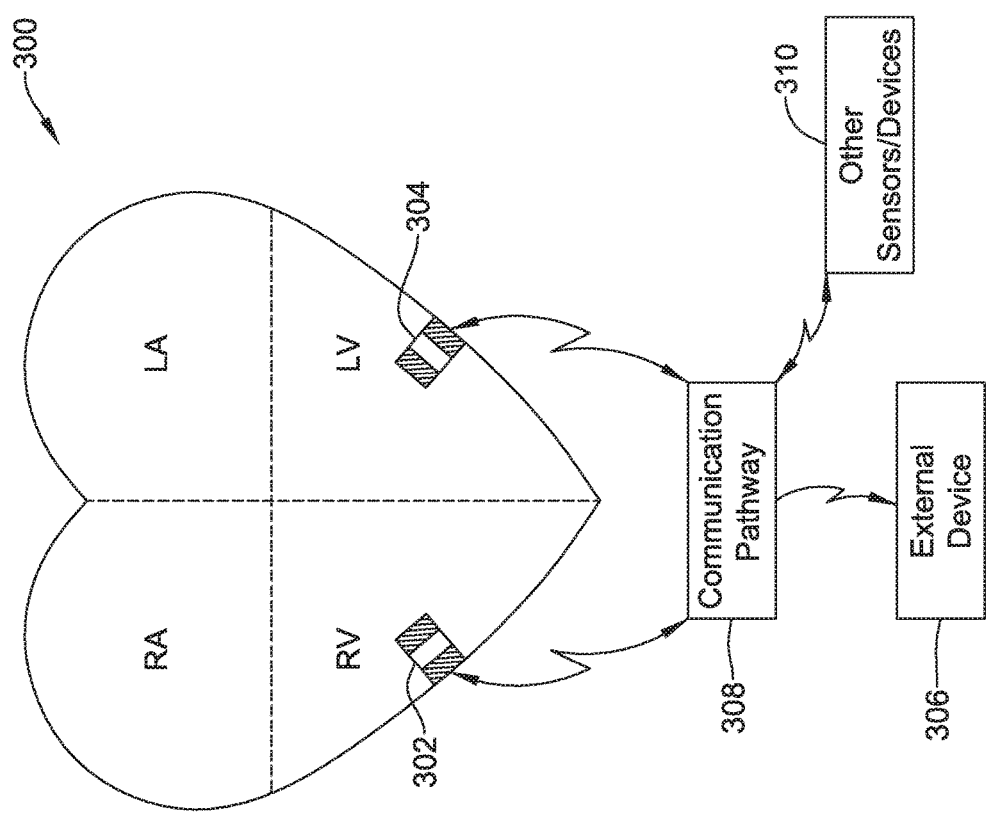
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses may have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired. In some cases, the delivered electrical communication pulses may be notches or other disturbances in a pacing pulse.

Unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
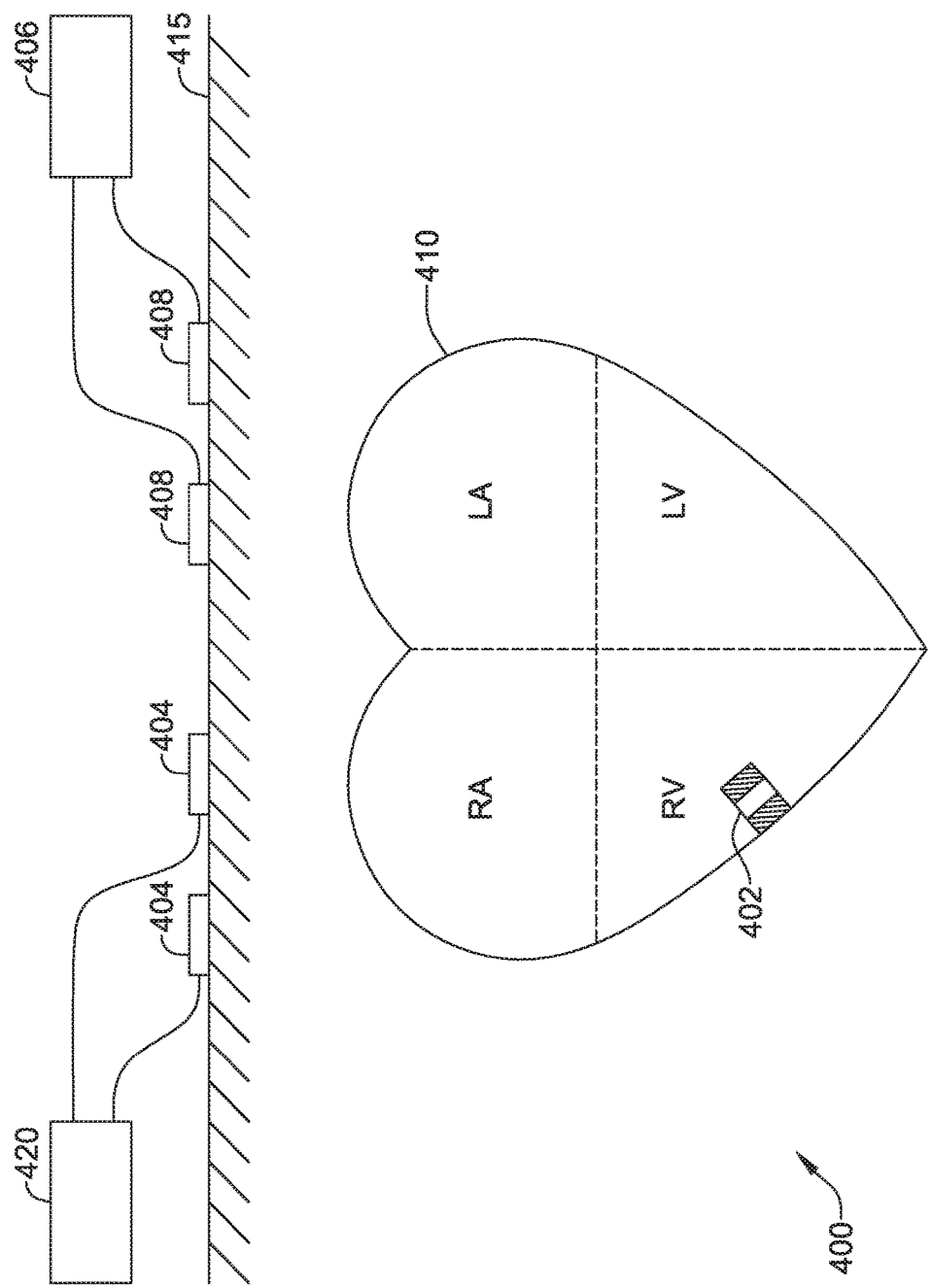
FIG. 4 is a schematic diagram of a medical device system including devices that are configured for conducted communication through the body.

FIG. 4 shows an illustrative medical device system 400 that may be configured to operate according to techniques disclosed herein. For example, the system may include multiple devices connected to a patient represented by heart 410 and skin 415, where at least some of the devices are configured for communication with other devices. In the exemplary system 400, an LCP 402 is shown fixed to the interior of the right ventricle of the heart 410, and external support device 420 and external defibrillator 406 are shown connected to skin 415 through skin electrodes 404 and 408, respectively. External support device 420 can be used to perform functions such as device identification, device programming and/or transfer of real-time and/or stored data between devices using one or more of the communication techniques described herein. In at least some embodiments, LCP 402 and external support device 420 are configured to communicate through conducted communication.

In some embodiments, external defibrillator 406 may be configured to deliver a voltage and/or current signal into the patient through skin 415 as a patch-integrity signal, and may further sense the patch-integrity signal in order to determine information about the contact between electrodes 408 and skin 415. External defibrillator 406 may be configured to display or emit an alarm if the received patch-integrity signal indicates insufficient contact between electrodes 408 and skin 415 to achieve sufficient sensing by the patch electrodes 408 of cardiac electrical signals of heart 410 and/or for safe delivery of defibrillation and/or cardioversion pulses. In some embodiments, the patch-integrity signal may represent a continuous signal, such as a sine-wave, square-wave, saw-tooth wave, or the like. Additionally, and in some cases, the patch-integrity signal may have a frequency of between about 50 kHz and about 150 kHz, but this is not required. In some instances, this patch-integrity signal may interfere with the conducted communication signals delivered and received by LCP 402 and external support device 420. Accordingly, the LCP 402 and/or external support device 420 may employ one or more techniques for enhancing the effectiveness of their conducted communication scheme, as described in more detail below.

It should be understood that the system of FIG. 4 is just one example system that may benefit from the techniques disclosed herein. Other system may include additional and/or different devices, but may still include a device delivering a conducted signal into the body of a patient that may interfere with conducted communication signals delivered into the patient's body for inter-device communication. Additionally, other systems may have different communication schemes that use additional communication modalities and/or include intermediary devices that receive conducted communication signals from a first device and relay received messages to a second device.

Figure 5:
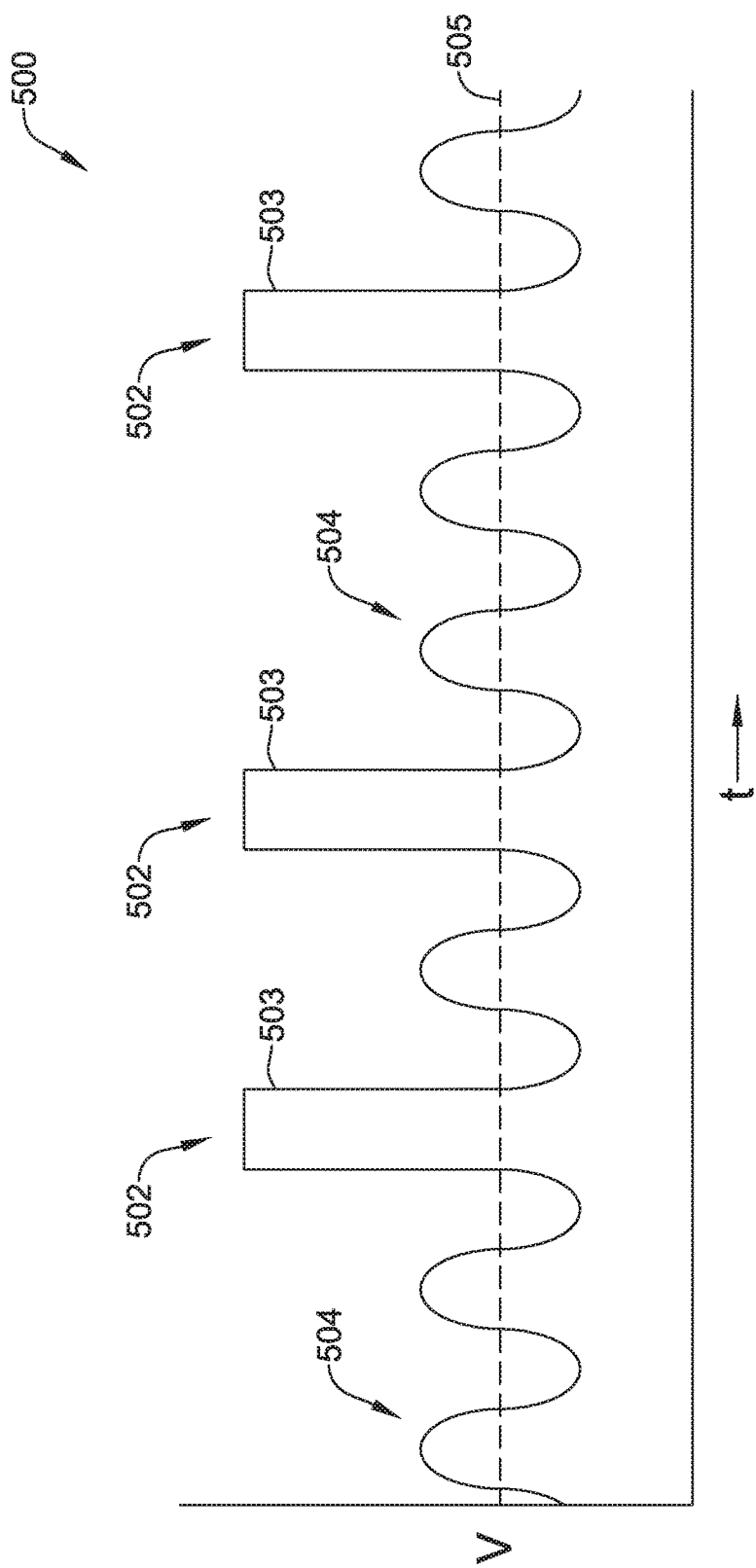
FIG. 5 depicts an example conducted communication signal sensed by a medical device including a noise component and a signal component.

FIG. 5 depicts an example conducted communication signal 500 that may be received by LCP 402. Although the description of the following examples uses external support device 420 as a transmitter and LCP 402 as a receiver, it should be understood that this is only for ease of description. The below described techniques may be implemented by any device of a system, such as system 400, with any of the devices of the system acting as the transmitter and any of the devices of the system acting as the receiver. This may include inter-device communication between, for example, two or more implanted medical devices, such as LCP 402 and another LCP (not shown in FIG. 4.) and/or other implanted device.

Figure 6:
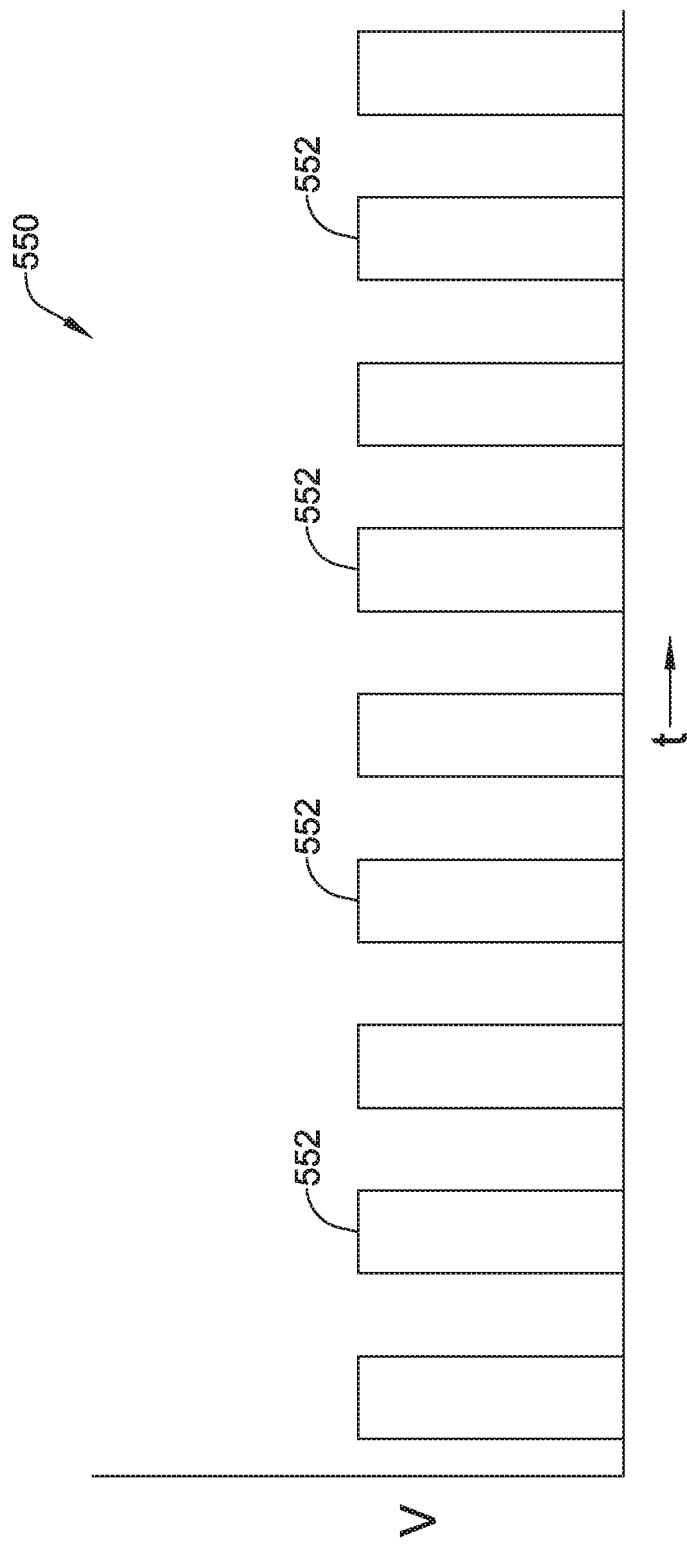
FIG. 6 depicts an example conducted communication signal after having been relayed through a comparator circuit having a first receive threshold, in accordance with techniques of the present disclosure.

In the example shown in FIG. 5, conducted communication signal 500 includes signal component 502 and noise component 504. In the example shown, signal component 502 represents a series of communication pulses 503 delivered by external support device 420 (or other internal or external device). In the example shown, noise component 504 represents a patch-integrity signal delivered by external defibrillator 406. Once LCP 402 receives the conducted communication signal, LCP 402 may perform initial amplification and/or filtering. Conducted communication signal 500 of FIG. 5 may represent the output of the initial amplification and/or filtering. LCP 402 may provide the conducted communication signal 500 to a comparator circuit, which may be part of a communication module of LCP 402. The comparator circuit may compare the conducted communication signal 500 to a receive threshold, such as a programmable receive threshold 505. In some cases, the comparator circuit may produce a pulse each time the conducted communication signal 500 is above the programmable receive threshold 505, resulting in a conducted communication signal 550 such as shown in FIG. 6. That is, in the example shown, the comparator circuit may generate a high signal (e.g. one of pulses 552) whenever the amplitude of conducted communication signal 500 is higher than the receive threshold 505.

As described, in some conducted communication schemes, the specific characteristics or spacing of received pulses, such as pulses 552 of conducted communication signal 550, may convey information. In some embodiments, LCP 402 and external support device 420 may be configured according to a specific communication protocol, whereby specific patterns of pulse characteristics and/or pulse spacing may represent predefined messages. Some example messages may include identification messages, commands, requests for data, and the like. If a received set of pulses do not have the characteristics that correspond to a recognized message format, the device may determine that a valid message has not been received, and conversely if a received set of pulses do have the characteristics that correspond to a recognized message formats, the device may determine that a valid message has been received.

In at least some instances, LCP 402 and/or external support device 420 may also determine whether a received message is valid by checking a received message for errors. For instance, the receiving device, even after receiving a series of pulses that correspond to a recognized message format, may employ one or more error checking schemes, such as repetition codes, parity bits, checksums, cyclic redundancy checks (CRC), or the like. When so provided, the device may only determine that a received message is valid if the error checking algorithm determines that there are no errors, or no significant errors, in the received message.

As can be seen in FIG. 6, conducted communication signal 550 includes pulses 552 generated from both signal component 502 and noise component 504 of conducted communication signal 500. Accordingly, and in some instances, LCP 402 may determine that conducted communication signal 550 is not a valid message as the pulse pattern will not match a recognized message format. In this example, receive threshold 505 is set too low such that portions of noise component 504 have an amplitude high enough to pass through the comparator circuit and generate pulses 552 in conducted communication signal 550.

Figure 7:
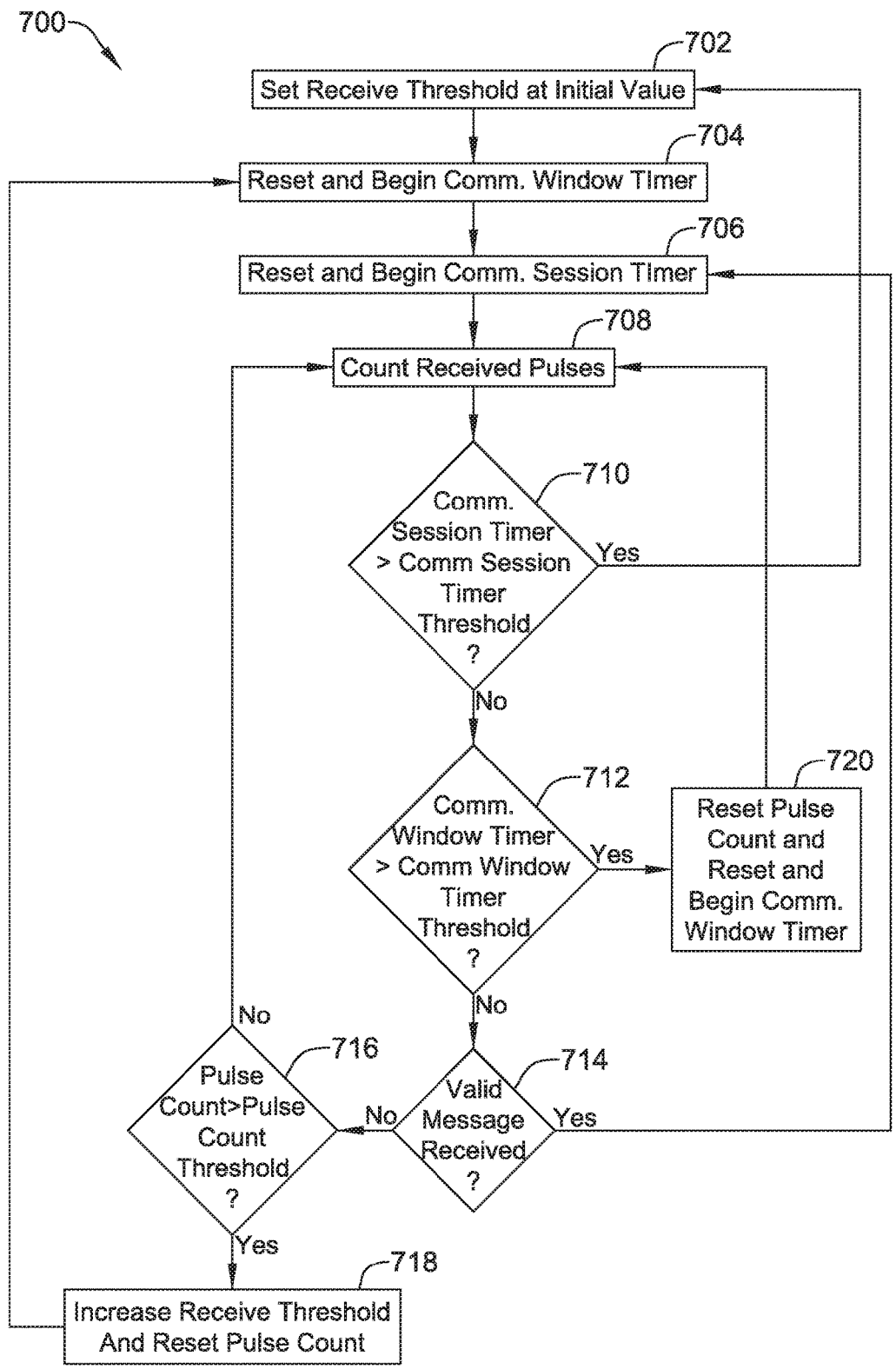
FIG. 7 is a flow diagram of an illustrative method that may be implemented by a medical device or medical device system, such as the illustrative medical devices and medical device systems described with respect to FIGS. 1-4.

FIG. 7 is a flow diagram of an illustrative method 700 that LCP 402 (or another device) may implement in order to adjust receive threshold 505 based, at least in part, on the amplitude of conducted communication signal 500. Adjusting receive threshold 505 to be above the amplitude of noise component 504 of conducted communication signal 500 may allow only signal component 502 to pass through the comparator circuit resulting in a conducted communication signal that only includes pulses due to signal component 502. This may produce a valid message received at LCP 402.

In the example method 700, LCP 402 may begin by setting receive threshold 505 to an initial value, as shown at 702. The initial value may be set such that, under most conditions, receive threshold 505 is below the amplitude of signal component 502 of conducted communication signal 500. Next, LCP 402 may reset and begin a communication window timer, as shown at 704, and reset and begin a communication session timer, as shown at 706. In some embodiments, LCP 402 may begin the communication window timer only at predefined times. For instance, the communication window timer may be synchronized to line up with one or more features of a sensed cardiac electrical signal, such as an R-wave. In such an example, once LCP 402 resets the communication window timer, LCP 402 may wait to start the communication window timer until sensing a particular feature in the cardiac electrical signal. In at least some instances, LCP 402 may start the communication window timer after a predefined time after sensing the particular feature. As one example, LCP 402 may wait between about 50 ms and about 150 ms after sensing an R-wave to begin the communication window timer.

In some cases, LCP 402 may count the number of received pulses in a received conducted communication signal, as shown at 708. For instance, received conducted communication signal 500 may be passed through the comparator circuit using receive threshold 505, resulting in conducted communication signal 550. As one example implementation, LCP 402 may increment a pulse count value every time LCP 402 detects a pulse in conducted communication signal 550.

Next, LCP 402 may determine whether the communication session timer has exceeded the communication session timer threshold, as shown at 710. If the communication session timer has exceeded the communication session timer threshold, LCP 402 may begin method 700 again back at 702. The communication session timer may help ensure that if receive threshold 505 ever gets set above the maximum amplitude of signal component 502 of conducted communication signal 500, receive threshold 505 is reset to a lower value. Although step 702 includes setting receive threshold 505 back to its initial value, in some instances, if LCP 402 arrives at step 702 through block 712, LCP 402 may set receive threshold 505 to a lower value that is different than the initial value. For instance, LCP 402 may simply reduce the value of receive threshold 505 instead of setting it back to its initial value.

If LCP 402 determines that the communication session timer has not exceeded the communication session timer threshold, LCP 402 may determine whether the communication window timer has exceeded the communication window timer threshold, as shown at 712. If LCP 402 determines that the communication window timer exceeded the communication window timer threshold, LCP 402 may reset the pulse count and reset and begin the communication window timer, as shown at 720, and then begin again with counting received pulses at 708.

If LCP 402 determines that the communication window timer does not exceed the communication window timer threshold, LCP 402 may determine whether a valid message was received, as shown at 714. For example, LCP 402 may compare the pattern of received pulses to predefined pulse patterns that represent messages. In some instances, LCP 402 may run one or more error checking schemes before or after determining whether the pattern of received pulses corresponds to one of the predefined pulse patterns. LCP 402 may determine that a valid message has been received after determining that the pattern of received pulses corresponds to one of the predefined pulse patterns, and if so provided, after determining that t there are no errors, or significant errors, in the received pulse pattern. If LCP 402 determines that a valid message has been received, LCP 402 may begin the method again at block 706, such as by following the 'YES' branch of block 714.

If no valid message has yet been received, LCP 402 may determine whether the pulse count is greater than the pulse count threshold, as shown at 716. The pulse count threshold may be set to above a maximum number of pulses that LCP 402 could possibly receive in a valid message. For instance, if each message may correspond to a predefined pulse pattern or sequence, there may be a maximum number of pulses that may be sent in a given message. Accordingly, if LCP 402 receives a number of pulses that is above the pulse count threshold within a communication window, LCP 402 may conclude that the conducted communication signal 550 has been corrupted by noise. Therefore, if LCP 402 determines that the pulse count has exceeded the pulse count threshold, LCP 402 may increase the value of receive threshold 505 and reset the pulse count, as shown at 718, and begin method 700 again at step 704. LCP 402 may increase the value of receive threshold 505 by a predetermined amount, based on how long it took for the number of received pulses to exceed the pulse count threshold, based on how much the number of received pulses exceeded the pulse count threshold, and/or based on any other suitable criteria. If the pulse count has not exceed the pulse count threshold, LCP 402 may loop back to step 708 and continue counting received pulses.

In some instances, LCP 402 may wait until the end of a communication window to determine whether a valid message was received and whether the pulse count exceeded the pulse count threshold. For instance, blocks 714 and 716 may be connected to the 'YES' branch block 712, such that LCP 402 only determines whether a valid message was received and whether the pulse count exceeded the pulse count threshold after the communication window timer exceeds the communication window timer threshold. Block 720 may then be connected to the 'NO' branch of block 716.

The LCP 402 may be configured to adjust receive threshold 505 based at least in part on the amplitude of conducted communication signal 500. Setting receive threshold 505 at an appropriate level effectively filters out noise component 504 in conducted communication signal 550. In operation, method 700 may work to increase receive threshold 505 above the peak amplitude of noise component 504 such that the peaks of noise component 504 are below receive threshold 505 such that the comparator circuit does not produce corresponding pulses in conducted communication signal 550. However, receive threshold 505 may remain below the peak amplitude of signal component 502, such that the comparator circuit does produce pulses in conducted communication signal 550 that correspond to the pulses in signal component 502.

Figure 8:
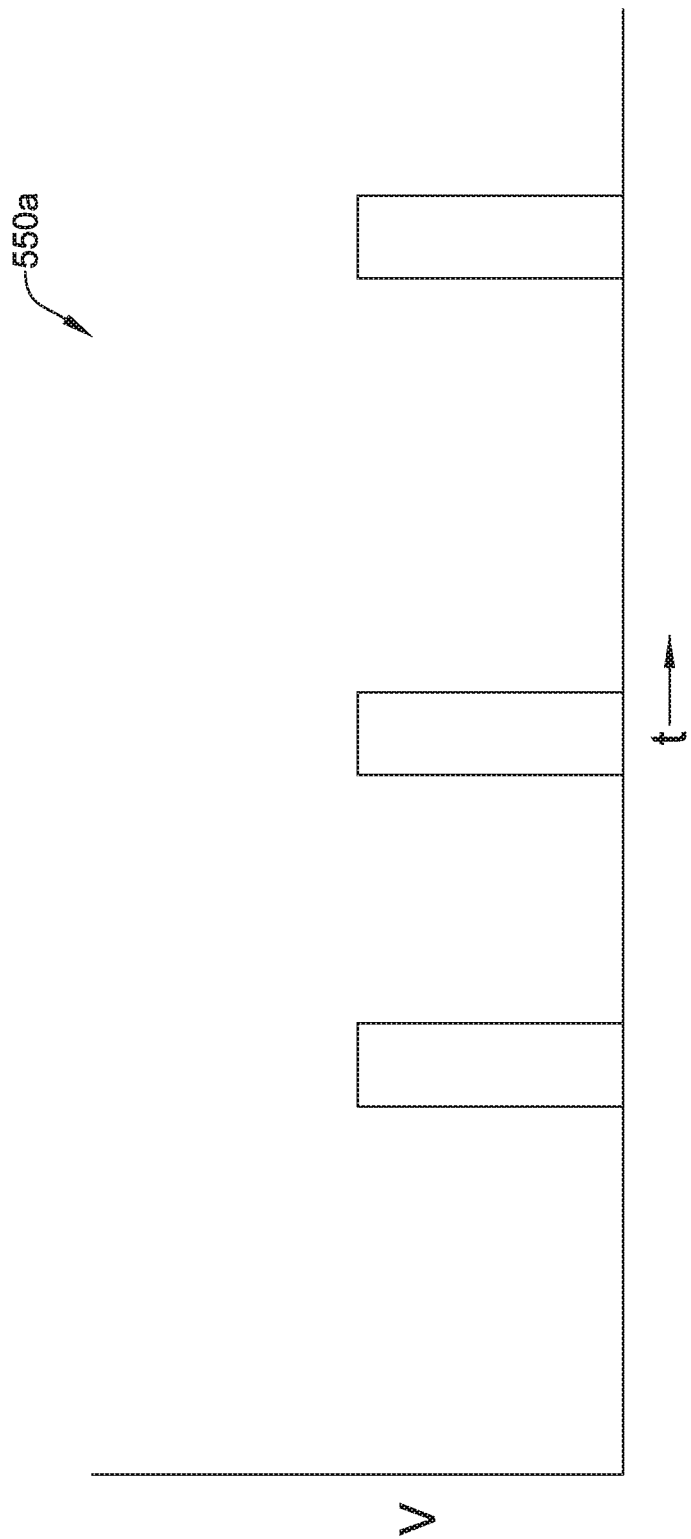
FIG. 8 depicts another example conducted communication signal after having been relayed through a comparator circuit with a second receive threshold, in accordance with techniques of the present disclosure.

FIG. 8 depicts conducted a communication signal 550a, which represents the output of the comparator circuit when the receive threshold 505 had been set higher than the maximum amplitude of noise component 504 but lower than the maximum amplitude of signal component 502. As can be seen, conducted communication signal 550 only includes pulses due to signal component 502 of conducted communication signal 500. When so provided, LCP 402 may interpret conducted communication signal 550a as a valid message.

Figure 9:
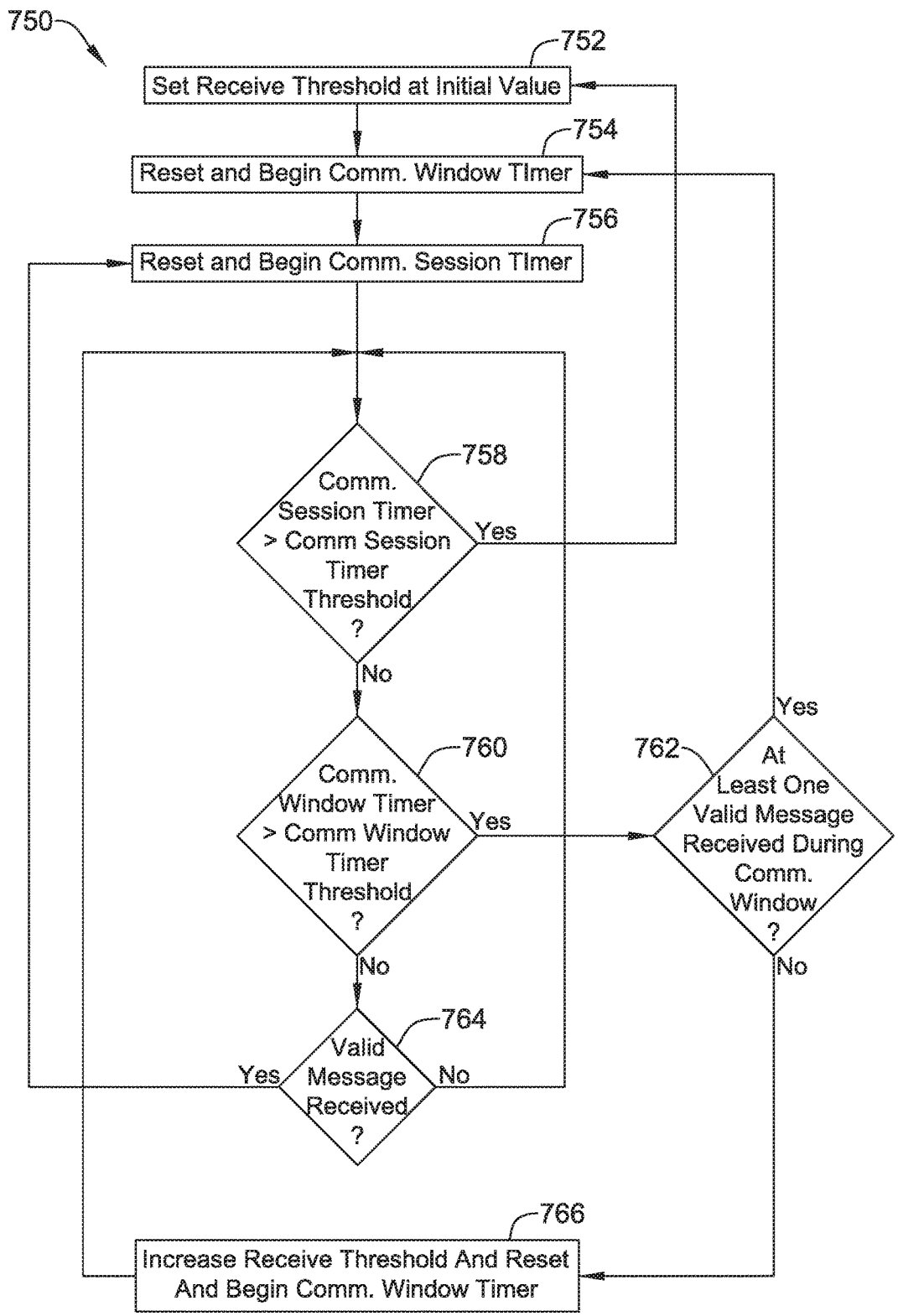
FIG. 9 is a flow diagram of an illustrative method that may be implemented by a medical device or medical device system, such as the illustrative medical devices and medical device systems described with respect to FIGS. 1-4.

FIG. 9 depicts a flowchart of another illustrative method 750 that LCP 402 (or another device) may use to adjust the receive threshold 505. In this case, the receive threshold 505 may be adjusted based, at least in part, on the amplitude of conducted communication signal 500. In the illustrative method 750, LCP 402 may receive regular messages from another device, such as external support device 420. In one example, at least one message may be received during each communication window.

LCP 402 may begin, as shown in method 700, by setting receive threshold 505 to an initial value, resetting and beginning a communication window timer, and resetting and beginning a communication session timer, as shown at 752, 754, and 756, respectively. Next, LCP 452 may determine whether the communication session timer has exceeded the communication session timer threshold, as shown at 758.

If LCP 402 determines that the communication window session timer has not exceeded the communication window session threshold, LCP 402 may determine whether the communication window timer has exceeded the communication window timer threshold, as shown at 760. If LCP 402 determines that the communication window timer has not exceeded the communication window timer threshold, LCP 402 may determine whether a valid message has been received, as a shown t 764. If no valid messaged has been received, LCP 402 may loop back to block 758. In this manner, LCP 402 may continue to check whether a valid message has been received during a communication window.

If LCP 402 determines that the communication window timer has exceeded the communication window timer threshold, LCP 402 may determine whether at least one valid messaged was received during the communication window. If no valid message was received, LCP 402 may increase receive threshold 505 and reset and begin the communication window timer, as shown at 766, and begin method 750 again at 758. LCP 402 may increase the value of receive threshold 505 by a predetermined amount, based on how long it took for the number of received pulses to exceed the pulse count threshold, or based on other criteria. If LCP 402 determines that at least one valid message has been received, LCP 402 may begin method 750 again at block 754.

In this manner, if receive threshold 505 is set too low, e.g. below the maximum amplitude of noise component 504, LCP 402 will not readily receive valid messages and will then increase the receive threshold 505. This will continue until receive threshold 505 is set above the amplitude of noise component 504 and LCP 402 may begin to receive valid messages based on only the signal component 502.

In some instances, LCP 402 may wait until after the communication window timer has exceeded the communication window timer threshold before determining whether a valid message has been received. For example, method 750 may not include block 764 at all. Instead, the 'NO' branch of block 760 may connect directly to block 756.

In some instances, LCP 402 may wait longer than a single communication window period before determining whether a pulse count exceeds a pulse count threshold or whether a valid message was received. For example, LCP 402 may wait until two, three, or even four communication windows have elapsed before making any determinations. These are just some example alternatives to the method shown in FIG. 9.

Figure 10:
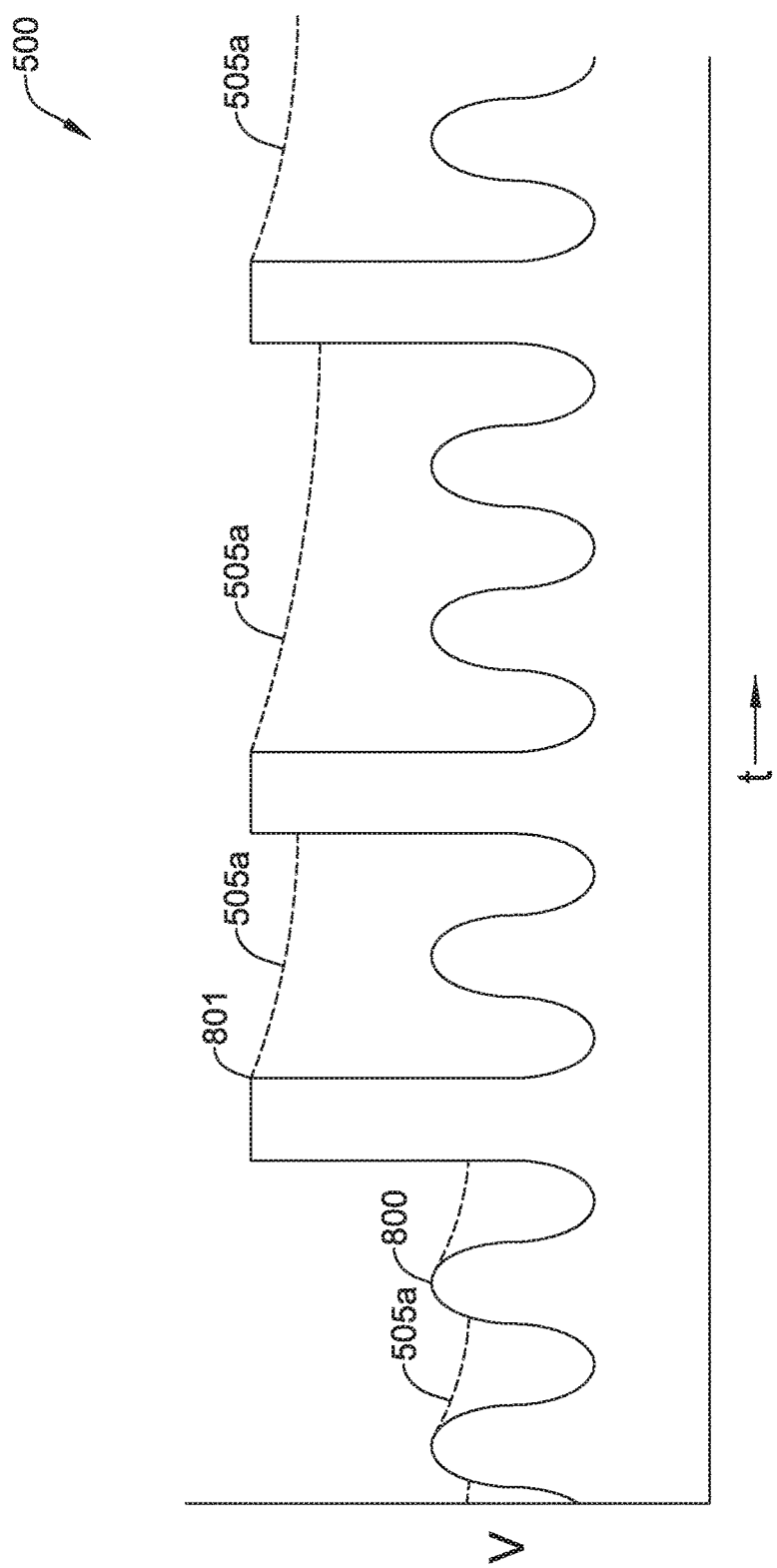
FIG. 10 depicts another example conducted communication signal along with a decaying receive threshold, in accordance with techniques of the present disclosure.

FIG. 10 depicts another method for adjusting the receive threshold 505. FIG. 10 depicts conducted communication signal 500 along with a dynamic receive threshold 505A, where the dynamic receive threshold 505A is reset to a new value on each of the peaks of conducted communication signal 500 that exceed the then present dynamic receive threshold 505A.

In the example of FIG. 10, dynamic receive threshold 505A may be set to an initial value and may be configured to decay over time to lower values. It should be understood that the decay shape of dynamic receive threshold 505A depicted in FIG. 10 is an example only. In one non-limiting example, dynamic receive threshold 505A may decay to about half of its initial value after 100 ms, and then decay to about one-quarter of its initial value over the subsequent 100 ms. The specific decay values and time periods may differ. It is contemplated that dynamic receive threshold 505A may decay in a logarithmic or natural logarithmic fashion, in an exponential fashion, in a step wise fashion, or any other desirable way.

As can be seen, dynamic receive threshold 505A is configured to decay after the conducted communication signal 500 reaches a peak amplitude that is above the then existing dynamic receive threshold 505A. For example, in FIG. 10, the dynamic receive threshold 505A begins to decay at peak 800 and at the end of peak 801. LCP 402 may reset the dynamic receive threshold 505A to a new higher value when conducted communication signal 500 reaches a new peak amplitude that is above the then existing dynamic receive threshold 505A. In some embodiments, LCP 402 may continually reset dynamic receive threshold 505A to a new, higher value as conducted communication signal 500 keeps providing peaks that exceed the decaying dynamic receive threshold 505A. As can be seen, once conducted communication signal 500 begins to drop in amplitude, dynamic receive threshold 505A will begin to decay. In some embodiments, dynamic receive threshold 505A may be configured to wait to decay for a short predefined time period after being set to a new value. In some cases, instead of continually resetting dynamic receive threshold 505A to a new, higher value, LCP 402 may wait to determine a peak of conducted communication signal 500. In some cases, resetting a new, higher value for dynamic receive threshold 505A may lag conducted communication signal 500 by a short period of time.

In some instances, instead of setting dynamic receive threshold 505A to the value of the most recent peak of conducted communication signal 500, LCP 402 may set dynamic receive threshold 505A to a value that is proportional to the most recent peak of conducted communication signal 500. For instance, LCP 402 may set dynamic receive threshold 505A to a value that is between 60%-99% of the maximum value of the most recent peak. This is just one example. Other examples include between 70%-99%, 80%-99%, or 90%-99% of the maximum value of the most recent peak of conducted communication signal 500.

In some cases, the decay characteristics of the dynamic receive threshold 505A may be based, at least partially, on the characteristics of the conducted communication signal 500. For example, dynamic receive threshold 505A may be configured to decay more quickly for higher values of the dynamic receive threshold 505A. In another example, dynamic receive threshold 505A may be configured to decay more quickly the longer it has been since the dynamic receive threshold 505A has been reset, which would correspond to a longer period of low amplitude activity of conducted communication signal 500. These are just examples.

In some alternative embodiments, LCP 402 may adjust the receive threshold to a value where LCP 402 detects that it successfully receives communication signals but does not receive noise signals. For instance, LCP 402 may initiate a search algorithm in order to adjust a receive threshold, such as threshold 505 or 505a. In some embodiments, the algorithm may have the receive threshold decay in a step-wise manner, and the time between decay steps may range from between about 4 ms to about 10,000 ms. The 4 ms value may represent the shortest length communication. The 10,000 ms value may represent a slow respiratory cycle which could impact a signal to noise ratio. However, in other embodiments, the time between decay steps may have any value between 4 ms and 10,000 ms. In some embodiments, the decay at each step may occur in binary ratios, such as 1/16, 1/32, 1/64, 1/128, or 1/256 or the like. For instance, at each decay step, receive threshold 505a may decay by the chosen 1/16 (or other chosen binary ratio) of the current value of receive threshold 505a. In further embodiments, the decay value may change at successive steps. For instance, the first decay amount may be 1/256 of receive threshold 505a, the second decay amount may be 1/128 of receive threshold 505a, the third decay amount may be 1/64 of receive threshold 505a, and the like. Once LCP 100 sets the receive threshold to a value where LCP 100 determines that it is receiving both a signal component and a noise component in received communication signals, LCP 100 may set the receive threshold to the previous value where LCP 100 did not detect both signal components and noise components in received communication signals. One particularly useful embodiments may include setting the time between decay steps at 25 ms and the decay value to 1/64. However, this is just one example.

In some cases, LCP 402 may employ an adaptive filter to help filter out noise component 504. As described, the patch-integrity signal of an external defibrillator 406 may be a continuous signal having generally static characteristics, such as frequency and/or amplitude. In such cases, LCP 402 may sense, outside of a communication period, the patch-integrity signal. LCP 402 may then process the patch-integrity signal to determine at least the frequency of the signal and may configure an adaptive filter into a notch filter centered at the frequency of the patch-integrity signal. In cases where patch-integrity signal has a single frequency, or a narrow frequency spectrum, the notch filter may be particularly effective in filtering out, or at least reducing in amplitude, the noise component 504.

Although the techniques were generally described separately, in instances, LCP 402 may employ multiple of the disclosed techniques simultaneously. For example, LCP 402 may implement the pulse-counting method described above in addition to a dynamic receive threshold. In another example, LCP 402 may implement the pulse counting method along with an adaptive filter. In general, in different embodiments, LCP 402 may include all combinations of the above described techniques.

It should be understood that although the above methods were described with LCP 402 as a receiver and external support device 420 as a transmitter, this was just for illustrative purposes. In some cases, external support device 420 may act as a receiver and may implement any techniques described with respect to LCP 402. Additionally, it should be understood that the described techniques are not limited to system 400. Indeed, the described techniques may be implemented by any device and/or system that uses conducted communication.

In some cases, one or more of the devices of system 400 (or other system) may be configured to actively cancel the patch-integrity signal. For instance, in the example of FIG. 4, instead of (or in addition to) devices of system 400 adjusting receive thresholds or adaptive filters, one or more of the devices of system 400 may inject a cancelling or inverse signal into the patient body in order to cancel out, or at least reduce the amplitude of, the patch-integrity signal delivered by external defibrillator 406. The below description uses external support device 420 only as an example of a device that may perform the described techniques. It should be understood, however, that the techniques described herein may be applied by any of the devices of system 400, or by other devices in other systems as desired.

FIG. 11A depicts an example patch-integrity signal 810 signal that may be delivered by an external defibrillator 406. External support device 420 may sense signals propagating through a patient's body, including patch-integrity signal 810, during a period of relative electrical quietness within the patient's body. For instance, external support device 420 may sense propagating electrical signals in the patient via electrodes 404 between heartbeats of the patient and while no conducted communication signals are propagating through the patient's body. Where patch-integrity signal 810 is sufficiently different from other signals propagating through the patient's body, external support device 420 may employ one or more filters to filter out signals other than patch-integrity signal 810, leaving only patch-integrity signal 810. For instance, external support device 420 may employ one or more low-pass, high-pass, bandpass, notch, and/or any other suitable filter. External support device 420 may determine various characteristics of patch-integrity signal 810. For instance, external support device 420 may determine the frequency components, the amplitude, and/or the phase of patch-integrity signal 810.

In some instances, external support device 420 may include a pulse generator module whereby external support device 420 may generate varied waveforms. After external support device 420 senses patch-integrity signal 810, external support device 420 may generate a cancelling or inverse signal 812 (see FIG. 11B) using the determined characteristics. For instance, external support device 420 may generate inverse signal 812 to have a similar amplitude and frequency as patch-integrity signal 810. However, external support device 420 may generate inverse signal 812 at a phase that is shifted relative to inverse signal 812 by one-hundred eighty degrees. An example of inverse signal 812 is depicted in FIG. 11B. If the patch-integrity signal 810 is not a regular signal as shown in FIG. 11A, the external support device 420 may simply generate an inverse signal 812 that will cancel out, or at least reduce the amplitude of, the patch-integrity signal 810. Other example inverse signals may include signals that are not true inverses of the patch-integrity signal. For instance, the inverse signal, when added to the patch-integrity signal, may reduce the amplitude of the patch-integrity signal received at a device of the system which includes external support device 420. Alternatively, the inverse signal, when added to the patch-integrity signal, may produce a signal that is received by a device of the system that include external support device 420 having an increased frequency than the original patch-integrity signal. This increased frequency of the patch-integrity signal may allow the signal to be more easily filtered out by the receiving device. Accordingly, although the description throughout this disclosure may focus on or discus an inverse signal that is a true inverse signal of the patch-integrity signal, or a close analog to a true inverse signal, it should be understood that this is merely for ease of description. In general, external support device 420 may generate an inverse signal that is not a true inverse signal, but interferes or changes the patch-integrity signal sufficiently to allow a receiving device to distinguish between the patch-integrity signal and communication signals or to filter the patch-integrity signal without filtering communication signals.

Figure 12:
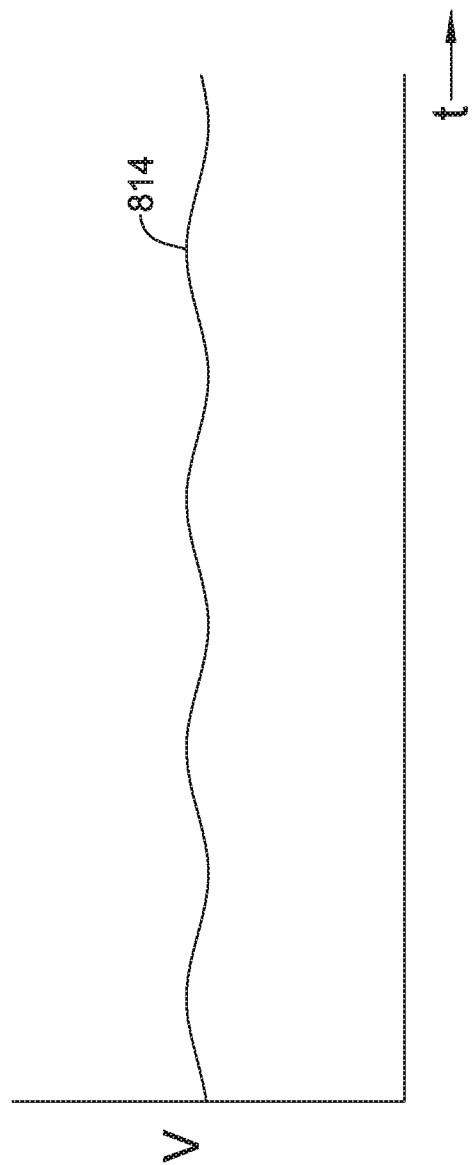
FIG. 12 depicts an example patch-integrity signal that may be sensed by a first medical device while a second medical device is delivering a cancelling or inverse signal, in accordance with techniques disclosed herein.

External support device 420 may deliver the generated inverse signal 812 into the body of the patient, for example through electrodes 404. Since inverse signal 812 has similar but opposite characteristics of patch-integrity signal 810, inverse signal 812 may destructively interfere with patch-integrity signal 810, thereby canceling out and/or at least reducing the amplitude of patch-integrity signal 810 sensed by other devices connected to the patient, such as LCP 402. In some examples, inverse signal 812 may be the exact opposite of patch-integrity signal 810 and may fully cancel inverse signal 812 such that LCP 402 does not sense patch-integrity signal 810. In other examples, inverse signal 812 may only be similar to patch-integrity signal 810 and may only reduce the amplitude of patch-integrity signal 810 sensed by LCP 402. In any case, the delivered inverse signal 812 may reduce the amplitude of patch-integrity signal 810 sensed by LCP 402, which can enhance the signal-to-noise ratio (SNR) of conducted communication between external support device 420 and LCP 402 (and/or between LCP 402 and another implanted devices). An example of a signal sensed by LCP 402 while external support device 420 is delivering inverse signal 812 is shown in FIG. 12 as signal 814.

In at least some embodiments, instead of attempting to match the amplitude of patch-integrity signal 810, external support device 420 may generate inverse signal 812 having a different amplitude than patch-integrity signal 810. The amplitude of patch-integrity signal 810 sensed by devices connected to the patient other than external support device 420, such as LCP 402, may differ than the amplitude of patch-integrity signal 810 sensed by external support device 420. Accordingly, delivering inverse signal 812 into the patient with an amplitude similar to patch-integrity signal 810 sensed by external support device 420 may cancel out patch-integrity signal 810 sensed by LCP 402, but may additionally introduce noise in the form of inverse signal 812, which was not fully cancelled out by patch-integrity signal 810. Accordingly, in some instances, external support device 420 may generate inverse signal 812 having an amplitude higher, or lower, than the amplitude of patch-integrity signal 810 sensed by external support device 420. External support device 420 may attempt to match the amplitude of inverse signal 812 sensed by LCP 402 to the amplitude of patch-integrity signal 810 sensed by LCP 402. For example, external support device 420 may adjust the amplitude of inverse signal 812 based on feedback received from LCP 402, or based on a presence or absence of received messages from LCP 402. In other embodiments, external support device 420 may include a physical dial or gain adjuster 424 that a user may adjust to increase or decrease the amplitude of generated inverse signal 812 (see FIG. 13).

Delivering inverse signal 812 into the patient's body may enhance the signal-to-noise ratio (SNR) of conducted communication with the body by removing or reducing the patch-integrity signal 810 in the body. In some embodiments, external support device 420 may deliver inverse signal 812 into the patient's body continuously. In other cases, the delivered inverse signal 812 may cause external defibrillator 406 to generate or emit an alarm as patch-integrity signal 810 sensed by external defibrillator 406 may be fully cancelled or reduced in amplitude below a certain alarm threshold. Accordingly, in some cases, external support device 420 may only selectively deliver inverse signal 812 into the patient's body. For example, external support device 420 may only deliver inverse signal 812 into the patient's body while external support device 420 or LCP 402 are delivering conducted communication signals into the patient's body. In some cases, LCP 402 may have an easier time discriminating between the delivered conducted communication signals from patch-integrity signal 810. In some cases, the conducted communication scheme of external support device 420 and LCP 402 may include only delivering conducted communication signals during predefined time periods. For instance, external support device 420 and LCP 402 may be configured to only deliver conducted communication signals during communication windows lasting about 100 ms, with each communication window separated by 800 ms. These numbers are just examples. The communication window lengths and spacing may be any suitable values.

In some cases, the communication windows may be synchronized to one or more features of the cardiac electrical signals. For instance, external support device 420 and LCP 402 may be configured to communication during communication windows that occur about 100-250 ms after each detected R-wave. External support device 420 may be configured to only deliver inverse signal 812 into the patient's body during these communication windows. Both external support device 420 and LCP 402 may benefit from enhanced discrimination between sensed conducted communication signals and patch-integrity signal 810.

The patch-integrity signal 810 depicted in FIG. 11A is only one example. Different external defibrillators currently on the market may use differently shaped patch-integrity signals. Accordingly, in some embodiments, instead of having a general waveform generator capable of generating any, or a large number of different types of waveforms, external support device 420 may include hardware or circuitry that may generate inverse signals of various different known patch-integrity signals used in available external defibrillators.

Figure 13:
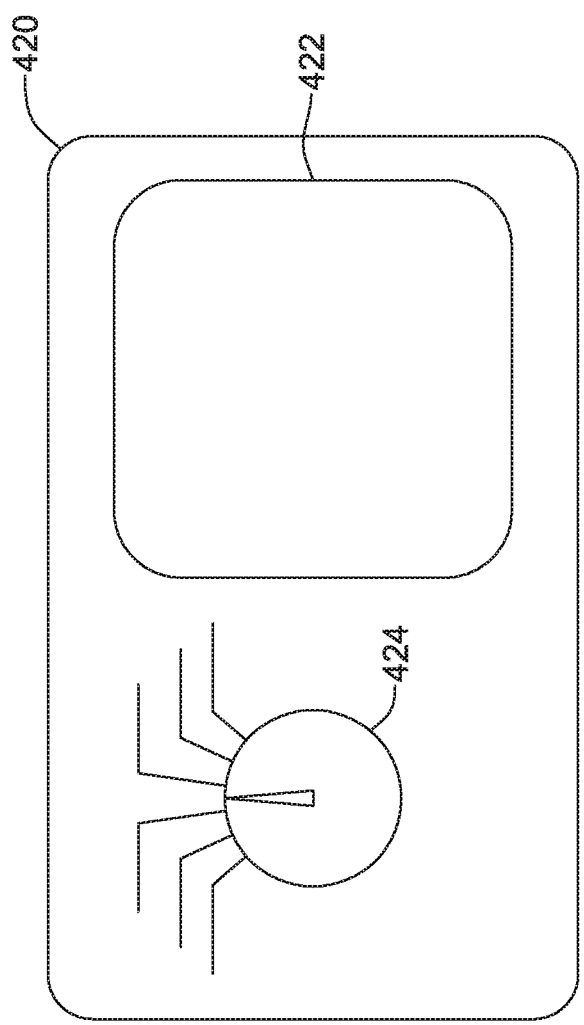
FIG. 13 is a schematic diagram of an example user interface that may be included on an external support device.

FIG. 13 depicts an example interface of an external support device 420. External support device 420 may include a dial, switch, or other mechanical selector, such as dial 424, or a menu option in graphical user interface 422, that allows a user to select a particular inverse waveform from a set of preprogrammed inverse waveforms that correspond to the different available external defibrillators. The preprogrammed inverse waveforms may be stored in a memory of external support device 420. Each selectable waveform may have an identifier correlating the waveform to a particular brand or product to easily identify the appropriate inverse waveform. These features may allow external support device 420 to be less complex and less costly to manufacture than when the external support device 420 is required to sense the patch-integrity signal and then generate an inverse signal using a general waveform generator.

Figure 14:
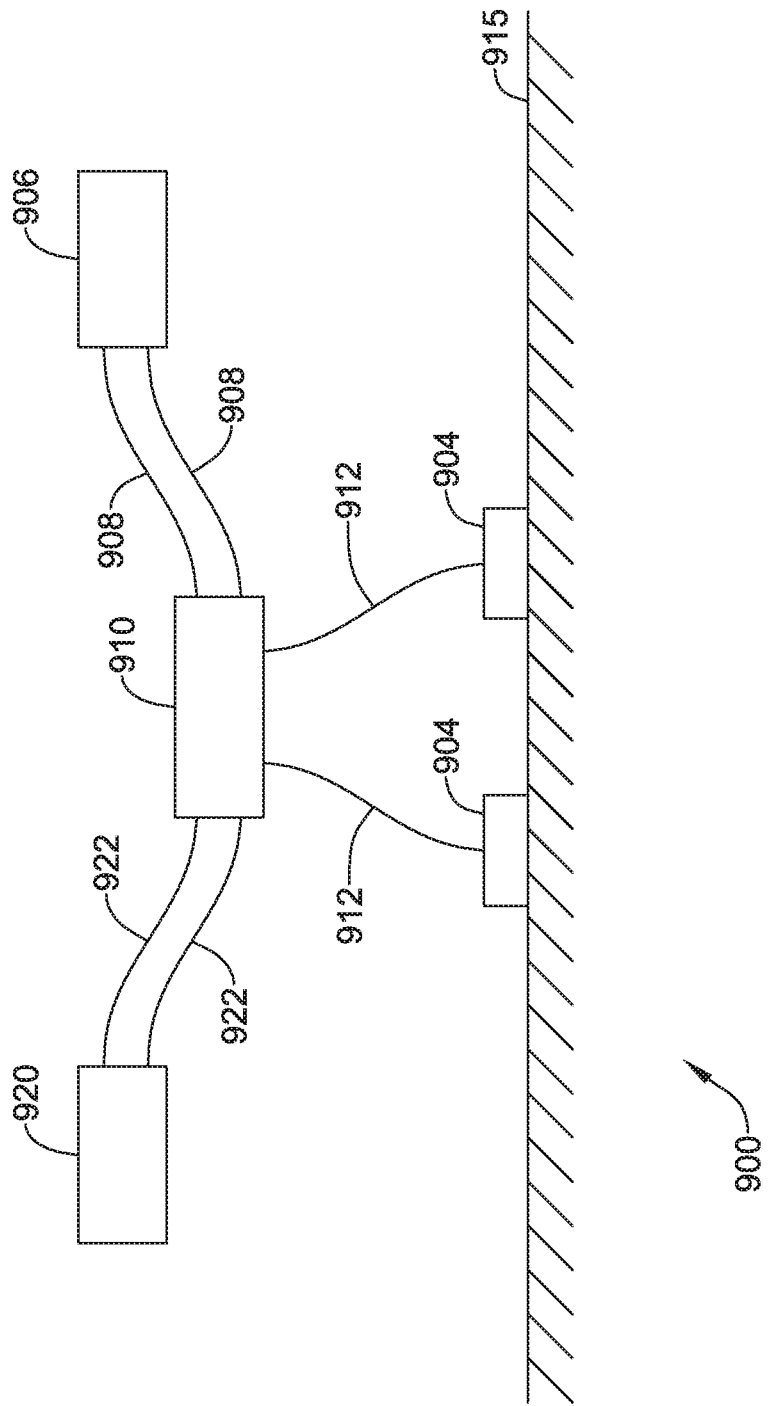
FIG. 14 is a schematic diagram of a medical device system for alternately connecting a first medical device and a second medical device to a pair of electrodes connected to a patient to enhance conducted communication through the patient, in accordance with techniques disclosed herein.

FIG. 14 depicts system 900 which may help enhance discrimination between conducted communication signals and noise signals such as patch-integrity signals. System 900 may include external support device 920, external defibrillator 906, and switching unit 910. External defibrillator 906 may be connected to switching unit 910 through wires 908, and external support device 920 may be connected to switching unit 910 by wires 922. Switching unit 910 may be connected to electrodes 904 attached to patient skin 915 through wires 912.

In system 900, a switching unit 910 may be configured to switch between wires 922 from external support device 920 and wires 908 from external defibrillator 906 to connect/disconnect each device to electrodes 904. Switching unit 910 may initially connect wires 908 to electrodes 904, allowing external defibrillator 906 to deliver a patch-integrity signal through electrode 904 and into the patient through skin 915. In some cases, when external support device 920 is to deliver conducted communication signals into the patient, switching unit 910 may disconnect wires 908 of external defibrillator 906 from the electrodes 904 and connect wires 922 from external support device 920 to the electrodes 904. In this configuration, external support device 920 may deliver conducted communication signals into the patient through electrodes 904. With the external defibrillator 906 disconnected from the electrodes 904, the patch-integrity signal is effectively blocked from entering the patient, and devices may communicate through conducted communication signals without interference from the patch-integrity signal. Once the conducted communication signals have been sent and received, switching unit 910 may disconnect wires 922 of the external support device 920 from the electrodes 904 and connect wires 908 of the external defibrillator 906 to the electrodes 904. The patch-integrity signal of the external defibrillator 906 may then be delivered to the patient, verifying to the external defibrillator 906 that the patch electrodes 904 are sufficiently in electrical communication with the skin. If the communication period is kept short enough, a patch verification alarm of the external defibrillator 906 may not be triggered.

In some instances, external support device 920 may control switching unit 910 to connect/disconnect wires 908, 922 from wires 912. In other instances, external defibrillator 906 may control switching unit 910, a different device may control switching unit 910, or both of external defibrillator 906 and external support device 920 may control switching unit 910. For ease of description, the techniques are described below from the perspective of external support device 920 controlling switching unit 910.

In operation, external defibrillator 906 may normally be connected to electrode 904 to deliver a patch-integrity signal and/or sense cardiac electrical signals. Before external support device 920 delivers conducted communication signals into the patient, external support device 920 may command switching unit 910 to disconnect wires 908 of the external defibrillator 906 from the electrodes 904 and connect wires 922 of the external support device 920 to the electrodes 904, thereby blocking the patch-integrity signal from external defibrillator 906 from being delivered to the patient. Once external support device 920 is finished delivering the conducted communication signals, external support device 920 may command switching unit 910 to reconnect wires 908 of the external defibrillator 906 to the electrodes 904.

In some instances, instead of only commanding switching unit 910 to connect wires 922 of the of the external support device 920 to the electrodes 904 before external support device 920 delivers conducted communication signals into the patient, external support device 920 may cause switching unit 910 to switch at regular intervals. For instance, in some cases where external support device 920 and another device, such as an LCP device, are connected to the patient and are configured to communicate using conducted communication only during predefined communication windows, external support device 920 may command switching unit 910 to connect wires 922 of the external support device 920 to the electrodes 904 during each of the communication windows.

When wires 908 of the external defibrillator 906 are disconnected from the electrodes 904, wires 908 may form an open circuit which may cause external defibrillator 906 to generate or emit an alarm, as external defibrillator 906 may no longer sense the patch-integrity signal. In some embodiments, in order help prevent external defibrillator 906 from generating an alarm, when switching unit 910 disconnects wires 908 of the external defibrillator 906 from the electrodes 904, switching unit 910 may connect wires 908 directly together, or may connect wires 908 together through a resistive or other network contained within switching unit 910. In these embodiments, switching unit 910 may maintain a closed loop for the patch-integrity signal, which may help prevent external defibrillator 906 from generating or emitting an alarm.

Although system 900 is depicted as including external defibrillator 906, switching unit 910, and external support device 920, it is contemplated that system 900 may include fewer or more devices. For instance, the support functions of external support device 920 and the switching functions of switching unit 910 may be built into external defibrillator 906. When so provided, external defibrillator 906 may have an internal switching mechanism and can control the switching mechanism to help support conducted communication via other devices within the patient.

In general, those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules. Accordingly, departure in form and detail may be made without departing from the scope and spirit of the present disclosure as described in the appended claims.

What is claimed is:

1. A method of communicating with a medical device implanted within a patient comprising:
   receiving, at a medical device via electrodes connected to the patient, a conducted communication signal, wherein the conducted communication signal comprises:
      a signal component that includes a plurality of communication pulses generated by a remote medical device; and
      a noise component;
   adjusting, by the medical device, a receive threshold based at least in part on an amplitude of the received conducted communication signal; and
   wherein adjusting the receive threshold at least partially reduces an amplitude of the noise component of the conducted communication signal.

2. The method of claim 1, wherein adjusting the receive threshold based at least in part on the amplitude of the received conducted communication signal comprises:
   counting, by the medical device, a number of pulses in the conducted communication signal that have an amplitude greater than the receive threshold during a communication window;
   determining, by the medical device, whether the counted number of pulses exceeds a pulse count threshold, wherein the pulse count threshold is based at least in part on a number of communication pulses that could occur in the signal component of the conducted communication signal during the communication window; and
   after determining the counted number of pulses exceeds the pulse count threshold, increasing, by the medical device, the receive threshold.

3. The method of claim 2, further comprising increasing the receive threshold by a predetermined amount.

4. The method of claim 2, wherein the pulse count threshold represents a maximum number of communication pulses that could occur in the signal component of the conducted communication signal during the communication window.

5. The method of claim 2, further comprising, after determining the counted number of pulses exceeds the pulse count threshold, beginning, by the medical device, a new communication window.

6. The method of claim 2, further comprising, by the medical device:
   tracking a communication session timer; and
   after determining the communication session timer has reached a threshold value, setting, by the medical device, the receive threshold to a lower predetermined value.

7. The method of claim 6, further comprising resetting, by the medical device, the communication session timer after successfully receiving a message.

8. The method of claim 1, wherein adjusting the receive threshold based at least in part on an amplitude of the received conducted communication signal comprises:
   after a communication window timer reaches a threshold value, determining, by the medical device, whether a message was received before the communication window timer reached the threshold value, wherein the message represents a predefined sequence of pulses in the conducted communication signal having an amplitude above the receive threshold; and after determining that no message was received before the communication window timer reached the threshold value, increasing, by the medical device, the receive threshold.

9. The method of claim 8, wherein increasing the receive threshold comprises increasing the receive threshold by a predetermined amount.

10. The method of claim 8, further comprising:
before the communication window timer has reached the threshold value, determining, by the medical device, whether a message has been received; and
after determining that a message has been received before the communication window timer has reached the threshold value, resetting, by the medical device, the communication window timer threshold value.

11. The method of claim 10, further comprising:
tracking, by the medical device, a communication session timer; and
after determining that the communication session timer has reached a threshold value, setting, by the medical device, the receive threshold to a lower predetermined value.

12. The method of claim 11, further comprising resetting, by the medical device, the communication session timer after determining that a message has been received.

13. The method of claim 1, wherein adjusting the receive threshold based at least in part on an amplitude of the received conducted communication signal comprises setting, by the medical device, the receive threshold to a value proportional to a maximum amplitude of a pulse of the conducted communication signal having an amplitude above the receive threshold.

14. The method of claim 13, wherein setting the receive threshold to a value proportional to the maximum amplitude of a pulse of the conducted communication signal having an amplitude above the receive threshold comprises setting the receive threshold to the maximum value of the amplitude of the pulse of the conducted communication signal having an amplitude above the receive threshold.

15. The method of claim 13, further comprising setting, by the medical device, the receive threshold to a value proportional to a maximum amplitude of each pulse of the conducted communication signal having an amplitude above the receive threshold.

16. The method of claim 13, wherein the receive threshold decays according to a predetermined function.

17. A medical device comprising:
one or more electrodes; and
a controller connected to the one or more electrodes, the controller configured to:
receive a conducted communication signal via the one or more electrodes, the conducted communication signal comprises:
a signal component that includes a plurality of communication pulses in a pulse pattern communicated from an external medical device; and
a noise component that includes noise signals; and
determine if the received conducted communication signal comprises one or more pulses that do not match the pulse pattern of the communication pulses, and when so, adjust a receive threshold to further filter out the noise signals from the received conducted communication signal.

18. The medical device of claim 17, wherein the controller is further configured to adjust the receive threshold by setting the receive threshold to a value proportional to a maximum amplitude of a pulse of the received conducted communication signal that exceeds the receive threshold.

19. The medical device of claim 17, wherein the receive threshold is configured to decay according to a predetermined decay function.

* * * * *